United States Patent [19]

Clark et al.

[11] Patent Number: 5,686,621
[45] Date of Patent: Nov. 11, 1997

[54] SUBSTITUTED HYDRINDANES FOR THE TREATMENT OF ANGIOGENESIS-DEPENDENT DISEASES

[75] Inventors: Abbot F. Clark, Arlington; Raymond E. Conrow, Fort Worth, both of Tex.

[73] Assignee: Alcon Laboratories, Inc., Fort Worth, Tex.

[21] Appl. No.: 468,680

[22] Filed: Jun. 6, 1995

Related U.S. Application Data

[60] Division of Ser. No. 209,325, filed as PCT/US93/07759 Aug. 17, 1993, Pat. No. 5,464,866, which is a continuation-in-part of Ser. No. 169,930, Dec. 20, 1993, abandoned, which is a continuation of Ser. No. 930,635, Aug. 17, 1992, abandoned.

[51] Int. Cl.$^6$ ................................................. A61K 31/27
[52] U.S. Cl. ................... 548/129; 548/300.1; 558/428; 560/31; 560/103; 562/500
[58] Field of Search .......................... 548/129, 300.1; 560/31, 103; 558/428; 562/500

[56] References Cited

U.S. PATENT DOCUMENTS 4,594,432  6/1986  Baggiolini et al. .................. 549/214
4,758,382  7/1988  Sterling et al. ..................... 260/397.2

FOREIGN PATENT DOCUMENTS 0516 410 A2  12/1992  European Pat. Off. .

OTHER PUBLICATIONS

BenEzra, "Neovasculogenic ability of prostaglandins, growth factors and synthetic chemoattractants," *American J. Ophthalmology*, 86:445–461, Oct. 1978.

Crum et al., "A new class of steroids which inhibits angiogenesis in the presence of heparin or a heparin fragment," *Science*, 230:375–378, 20 Dec. 1985.

Doctrow & Kulakowski, "Angiogenesis modulators—New drugs for controlling blood vessel growth?" *Drug News & Perspectives* 2:74–81, Mar., 1989.

Folkman et al., "Angiogenic factors," *Science* 235:442–447, 1987.

Furcht, "Critical factors controlling angiogenesis: cell products, cell matrix and growth factors," *Laboratory Investigation*, 55:505–509, 1986.

Ingber & Folkman, "Inhibition of Angiogenesis through modulation of collagen metabolism," *Laboratory Investigation*, 59:44–51, 1988.

Ingber et al., "Synthetic analogues of fumagillin that inhibit angiogenesis and suppress tumor growth," *Nature*, vol. 348:555–557, 6 Dec. 1990.

Javier Sardina, F., et al., *J. Org. Chem.* 51:1264, 1986.

Johnson, W.S., et al., *J. Am. Chem. Soc.* 106:1138, 1984.

Johnson, W.S. et al., *J. Org. Chem.* 50:2598, 1985.

Li et al., "Angiostatic steroids potentiated by sulphated cyclodextrin inhibit corneal neovascularization," *Investigative Ophthalmology and Visual Science*, 32:2898–2905, Oct. 1991.

Maione & Sharpe, "Development of angiogenesis inhibitors for clinical applications," *Trends in Pharmaceutical Sciences*, 11:457–461, Nov. 1990.

Maione et al., "Inhibition of angiogenesis by human platelet factor–4 and related peptides," *Science*, 247:77–79, 5 Jan. 1990.

McNatt et al., "Angiostatic activity and metabolism of cortisol in the chorioallantoic membrane (CAM) of the chick embryo," *J. Steroid Biochem. Molec. Biol.* vol. 42:687–693, 1992.

Oikawa et al., "A highly potent antiangiogenic activity of retinoids," *Cancer Letters*, 48:157–162, 1989.

Oikawa et al., "Powerful antiangiogenic activity of herbimycin A," *The Journal of Antibiotics*, XLII:1202–1204, Jul., 1989.

Oikawa et al., "Inhibition of angiogenesis by vitamin $D_3$ analogues," *European J. Pharmacology*, 178:247–250, 1990.

*Primary Examiner*—Brian M. Burn
*Attorney, Agent, or Firm*—Patrick M. Ryan

[57] ABSTRACT

Substituted hydrindanes and their use in controlling angiogenesis-dependent diseases in warm blooded animals are disclosed.

4 Claims, No Drawings

SUBSTITUTED HYDRINDANES FOR THE TREATMENT OF ANGIOGENESIS-DEPENDENT DISEASES

This is a divisional application of U.S. patent application Ser. No. 08/209,325 filed Mar. 10, 1994, (now U.S. Pat. No. 5,464,866) which is a continuation-in-part of co-pending international application number PCT/US93/07759 filed Aug. 17, 1993, which is a continuation-in-part of application Ser. No. 08/169,930 filed Dec. 20, 1993, (now abandoned) which is a continuation of application Ser. No. 07/930,635 filed Aug. 17, 1992, now abandoned.

BACKGROUND OF THE INVENTION

1. Field of Invention

This invention is directed to substituted hydrindanes and their use in preventing and treating angiogenesis-dependent diseases in warm blooded animals.

2. Description of Related Art

Angiogenesis refers to the generation and growth of new blood vessels and is often referred to as neovascularization. A number of compounds have been shown to inhibit angiogenesis. PF4 and its derivatives (Malone, et al., "Inhibition of angiogenesis by recombinant human platelet factor-4 and related peptides," Science, 247:77–79, 5 Jan. 1990), inhibitors of collagen synthesis (Ingber & Folkman, "Inhibition of Angiogenesis through modulation of collagen metabolism," Laboratory Investigation, 59:44–51, 1988), synthetic analogs of fumagillin (Ingber, et al., "Synthetic analogues of fumagillin that inhibit angiogenesis and suppress tumor growth," Nature, Vol. 348:555–557, 6 Dec. 1990), retinoids (Oikawa, et al., "A highly potent antiangiogenic activity of retinoids," Cancer Letters, 48:157–162, 1989), herbimycin A (Oikawa, et al., "Powerful antiangiogenic activity of herbimycin A," The Journal of Antibiotics, XLII1202–1204, July, 1989), vitamin D analogs including calcitriol (Oikawa, et al, "Inhibition of angiogenesis by vitamin $D_3$ analogues," European J. Pharmacology, 178:247–250, 1990), and angiostatic steroids in the presence of a heparin cofactor (Crum, et al., "A new class of steroids which inhibits angiogenesis in the presence of heparin or a heparin fragment," Science, 230:375–378, 20 Dec. 1985) have been demonstrated to inhibit angiogenesis in the chick embryo chorioallantoic membrane (CAM) model of neovascularization. Topical ocular administration of angiostatic steroids in a cyclodextrin formulation inhibits lipopolysaccharide induced corneal neovascularization in the rabbit (Li, et al., "Angiostatic steroids potentiated by sulphated cyclodextrin inhibit corneal neovascularization," Investigative Ophthalmology and Visual Science, 32:2898–2905, October, 1991).

SUMMARY OF INVENTION

This invention is directed to substituted hydrindanes useful in the inhibition of neovascularization. These compounds can be used in the treatment of angiogenesis-dependent diseases. These compounds are particularly useful for the treatment and control of angiogenesis associated with ocular neovascular diseases, solid tumor growth, diabetes and arthritis.

This invention is also directed to methods for controlling and preventing angiogenesis dependent diseases through the systemic or local administration of the compositions herein disclosed.

DETAILED DESCRIPTION OF PREFERRED EMBODIMENTS

The development and formation of new blood vessels for the purpose of sustaining vital tissue is known as angiogenesis or neovascularization. Angiogenesis is a very important process in the development of an organism; however, a large number of diseases are associated with the aberrant growth of new blood vessels. These diseases are referred to as angiogenesis dependent diseases. The substituted hydrindanes of the present invention are useful in preventing and treating, collectively referred to herein as "controlling," neovascularization associated with disease in warm blooded animals, including humans.

Two classes of compounds which are known to inhibit angiogenesis in the chick embryo chorioallantoic membrane (CAM) model of neovascularization are angiostatic steroids, such as tetrahydrocortexolone, and dihydroxy-vitamin D analogs, such as calcitriol. Vitamin D is a steroid in which the B ring of the steroid nucleus is photochemically cleaved (i.e. a B-seco steroid).

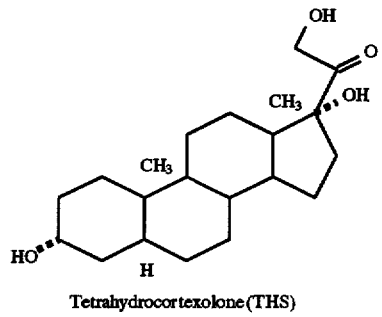

Tetrahydrocortexolone (THS)

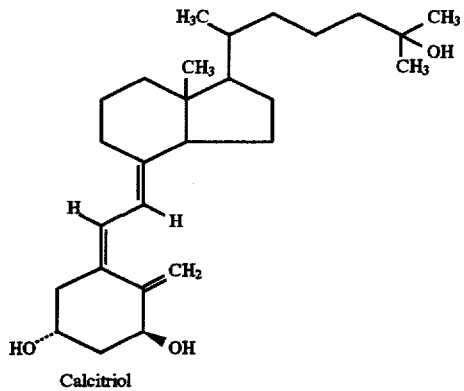

Calcitriol

Our structure-activity relationship studies of angiostatic steroids and vitamin D analogs in the chick CAM model of neovascularization allowed us to predict that certain fragments of angiostatic steroids or vitamin D analogs would be angiostatic (i.e. inhibit neovascularization). Compounds lacking the A and B rings of the steroid nucleus and containing the six carbon C ring and the five carbon D ring (i.e. substituted hydrindanes) were prepared and evaluated for angiostatic activity in the chick CAM model (details of the methods of the CAM assay may be found in McNatt, et al., Angiostatic activity and metabolism of cortisol in the chorioallantoic membrane (CAM) of the chick embryo J. Steroid Biochem. Molec. Biol. Vol. 42:687–693, 1992). These substituted hydrindanes had angiostatic activity 1000–10,000 times as potent as angiostatic steroids tested in this system.

The substituted hydrindanes of the present invention have the following formula:

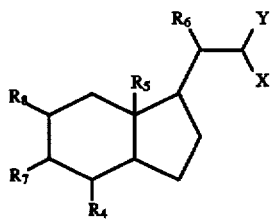

where X is OH, $OR_1$, $OR_2$, $OS(O)_2R_3$, $ON=CHR_1$, $ON=CR_1R_1$, CN, $R_1$, $R_2$, $CH(OH)R_2$, $CH(OR_1)OR_2$, $CH(OR_2)R_2$, $C(OH)R_1R_1$, $C(OR_1)R_1R_1$, $C(OR_2)R_1R_1$, $C(OH)R_1R_2$, $C(OR_1)R_1R_2$, $C(OR_2)R_1R_2$, $C(OH)R_2R_2$, $C(OR_1)R_2R_2$, $C(OR_2)R_2R_2$, $S(=O)_nH$, $S(=O)_nR_1$, $SR_2$, $P(=O)R_1R_1$, $P(=O)(OH)_2$, $P(=O)(OH)(OR_1)$, $P(=O)(OR_1)(OR_1)$, $P(=O)(OH)(NH_2)$, $P(=O)(OR_1)(NH_2)$, $P(=O)(OH)(NHR_1)$, $P(=O)(OH)(NR_1R_1)$, $P(=O)(OR_1)(NHR_1)$ $P(=O)(OR_1)(NR_1R_1)$, $NH_2$, $NHR_1$, $NHR_2$, $NR_1R_1$, $NR_1R_2$, NHOH, $N(OH)R_1$, $N(OH)R_2$, $NH(OR_1)$, $NH(OR_2)$, $N(OR_1)R_2$, $N(OR_2)R_1$, $N(OR_2)R_2$, $N(OR_1)R_1$, $^{\oplus}S(R_1)(R_1)$ $Q^{\oplus}$, $^{\oplus}N(R_1)(R_1)(R_1)$ $Q^{\oplus}$ wherein $Q^{\oplus}$ is a halide, sulfonate, or carboxylate anion; $C(=O)R_1$, $O=O)R_2$, $C(=O)NH_2$, $C(=O)NHR_1$, $C(=O)NR_1R_1$, $C(=O)N(OH)R_1$, $C(=O)N(OR_1)R_1$, $O=O)N(OR_2)R_1$; or

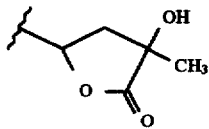

n=0, 1 or 2;

$R_1$ is aryl, haloaryl, $C_1-C_{10}$ alkyl, branched alkyl, cycloalkyl, aralkyl, carboxyalkyl or haloalkyl, optionally unsaturated and/or substituted with up to 6 OH, 6 $OR_3$, or 6 $OR_2$; or imidazolyl, triazolyl, thiadiazolyl, oxadiazolyl, thiazolyl, isothiazolyl, oxazolyl, isoxazolyl, or pyridyl, optionally substituted with up to three halogen or $C_1-C_6$ alkyl groups;

$R_2$ is $C(=O)H$, $C(=O)R_1$, $C(=O)OR_1$, $C(=O)OH$, $C(=O)NH_2$, $C(=O)NHR_1$, $C(=O)NR_1R_1$;

$R_3$ is aryl, haloaryl, $C_1-C_{10}$ alkyl, branched alkyl, cycloalkyl, aralkyl, carboxyalkyl or haloalkyl optionally unsaturated and/or substituted with up to 6 OH;

$R_4$ is H, (=O), $OR_2$, $OR_1$, OH, =NOH, =$NOR_1$, =$NOR_2$;

$R_5$ and $R_6$ are independently H, $CH_3$ or $CH_2CH_3$;

Y is H, OH, $OR_1$, $OR_2$ or (=O), with the proviso that if Y is OH, then X is $R_1$, $R_2$, $CH(OH)R_2$, $CH(OR_1)R_2$, $CH(OR_2)R_2$, $C(OH)R_1R_2$, $C(OR_1)R_1R_2$, $C(OR_2)R_1R_2$, $C(OH)R_2R_2$, $C(OR_1)R_2R_2$, $C(OR_2)R_2R_2$, and if Y is (=O) then X is $R_1$, $R_2$, $CH(OH)R_2$, $CH(OR_1)R_2$, $CH(OR_2)R_2$, $C(OH)R_1R_2$, $C(OR_1)R_1R_2$, $C(OR_2)R_1R_2$, $C(OH)R_2R_2$, $C(OR_1)R_2R_2$, $C(OR_2)R_2R_2$, $NH_2$, $NHR_1$, $NR_1R_1$, NHOH, $N(OH)R_1$, $NH(OR_1)$, $NH(OR_2)_2$, $N(OR_1)R_1$, or $N(OR_2)R_1$; and $R_7$ and $R_8$ are independently H or $C_1$ to $C_6$ alkyl, branched alkyl, hydroxyalkyl, optionally unsaturated; or $R_7$ and $R_8$ together form a double bond.

$R_1R_1$ attached to the same C, S, P or N atom can form a ring of from 3 through 7 members; and for those substituents containing more than one $R_1$, $R_2$, or $R_3$, each $R_1$, $R_2$, or $R_3$ may be the same or different.

Unless otherwise specified, all substituent groups can be attached to the hydrindane ring system in either the alpha or beta position. Additionally, the above structures include all pharmaceutically acceptable salts and esters of the substituted hydrindanes.

Compounds of Formula 1 having the following structure are preferred (Formula 2):

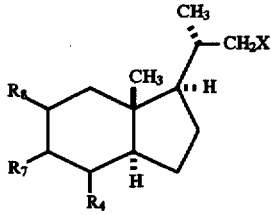

where X is $C(OH)R_1R_1$, $C(OR_1)R_1R_1$, $C(OR_2)R_1R_1$, $C(OH)R_1R_2$, $C(OR_1)R_1R_2$, $C(OR_2)R_1R_2$, $C(OH)R_2R_2$, $C(OR_1)R_2R_2$, $C(OR_2)R_2R_2$, $S(=O)_nH$, $S(=O)_nR_1$, $SR_2$, $P(=O)R_1R_1$, $P(=O)(OH)_2$, $P(=O)(OH)(OR_1)$, $P(=O)(OR_1)(OR_1)$, $P(=O)(OH)(NH_2)$, $P(=O)(OR_1)(NH_2)$, $P(=O)(OH)(NHR_1)$, $P(=O)(OH)(NR_1R_1)$, $P(=O)(OR_1)(NHR_1)$ $P(=O)(OR_1)(NR_1R_1)$, $NH_2$, $NHR_1$, $NHR_2$, $NR_1R_1$, $NR_1R_2$, NHOH, $N(OH)R_1$, $N(OH)R_2$, $NH(OR_1)$, $NH(OR_2)$, $N(OR_1)R_2$, $N(OR_2)R_1$, $N(OR_2)R_2$, $N(OR_1)R_1$, $^{\oplus}S(R_1)(R_1)(R_1)$ $Q^{\oplus}$ where $W^{\oplus}$ is a halide, sulfonate, or carboxylate anion; $C(=O)R_1$, $C(=O)R_2$, $C(=O)NH_2$, $C(=O)NHR_1$, $C(=O)NR_1R_1$, $C(=O)N(OH)R_1$, $C(=O)N(OR_1)R_1$, $C(=O)N(OR_2)R_1$;

n =0, 1 or 2;

$R_1$ is aryl, haloaryl, $C_1-C_{10}$ alkyl, branched alkyl, cycloalkyl, aralkyl, carboxyalkyl or haloalkyl, optionally unsaturated and/or substituted with up to 6 OH, 6 $OR_3$, or 6 $OR_2$; or imidazolyl, triazolyl, thiadiazolyl, oxadiazolyl, thiazolyl, isothiazolyl, oxazolyl, isoxazolyl, or pyridyl, optionally substituted with up to three halogen or $C_1-C_6$ alkyl groups;

$R_2$ is $C(=O)H$, $C(=O)R_1$, $C(=O)OR_1$, $C(=O)OH$, $C(=O)NH_2$, $C(=O)NHR_1$, $C(=O)NR_1R_1$;

$R_3$ is aryl, haloaryl, $C_1-C_{10}$ alkyl, branched alkyl, cycloalkyl, aralkyl, carboxyalkyl or haloalkyl optionally unsaturated and/or substituted with up to 6 OH;

$R_4$ is H, $OR_2$, $OR_1$, OH, =NOH, =$NOR_1$, =$NOR_2$; and provided that if X is $S(O)_2$(optionally substituted phenyl) then $R_4 \neq$OH; and $R_7$ and $R_8$ are H or together are optionally a double bond; and wherein aryl denotes phenyl, naphthyl, furyl, thienyl, pyridyl, benzofuryl, indolyl, benzothienyl, quinolyl or isoquinolyl;

$R_1R_1$ attached to the same C, S, P or N atom can form a ring of from 3 through 7 members; and for those substituents containing more than one $R_1$, $R_2$, or $R_3$, each $R_3$, $R_2$, or $R_3$ may be the same or different.

More preferred compounds are compounds of Formula 2 where the stereochemistry is as specified below.

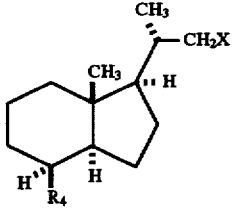

where X and $R_4$ are the same as above.

Especially preferred are De-A,B-26-(benzoyloxy)-25-methyl-23-thiacholestan-8β-ol-23-dioxide-8β(4-bromophenyl) carbamate, De-A,B-24-phenyl-23-thiacholan-8β-ol-23-dioxide-8β-(4-bromophenyl) carbamate, and De-A,B-23-thiacholestan-8β,25-diol-23-dioxide-8β,25-bis(4-bromophenyl) carbamate.

The compounds of Formula 2 can be prepared from diol 3a. Stereoisomers of compounds of Formula 2, as well as related compounds of Formula 1 having substituents $R_5 \neq CH_3$ and $R_6 \neq CH_3$, can be prepared by total synthesis using appropriately modified materials and procedures, and/ or in some cases from materials (e.g. Compound 3a) derived from Vitamin $D_2$, at the discretion of one skilled in the art.

The compounds of Formula 2 can be prepared starting with the known "Inhoffen-Lythgoe diol" 3a which can be prepared from Vitamin $D_2$. Alternatively, 3a can be prepared by total synthesis, for example, as described in: Wovkulich et al., *Tetrahedron* 40:2283 (1984), or in: Johnson et al., *J. Am. Chem. Soc.* 106: 1138 (1984).

Conversion of the primary hydroxyl group of diol 3a to a good leaving group, as in the known monotosylate 3b, allows the preparation of thioether and amine derivatives of hydrindanes. For example, reaction of 3b with benzyl mercaptan and a base produces benzyl thioether 3c. Compound 3c can be treated with an

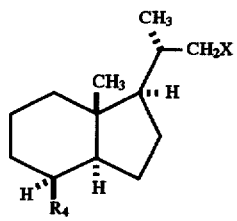

3a, $R_4$=OH, X=OH
3b, $R_4$=OH, X=OTs
3c, $R_4$=OH, X=SCH$_2$Ph
3d, $R_4$=OC(=O)NHC$_6$H$_4$Br-p, X=SCH$_2$Ph
3e, $R_4$=OC(=O)NHC$_6$H$_4$Br-p, X=S(O)$_2$CH$_2$Ph
3f, $R_4$=OH X=SH
3g $R_4$=OH, X=SCH$_2$C(CH$_3$)$_2$OH
3h, $R_4$=OC(=O)NHC$_6$H$_4$Br-$_p$, X=OTs
3j, $R_4$=OC(=O)NHC$_6$H$_4$Br-p, X=SH
3k, $R_4$=OC(=O)NHC$_6$H$_4$Br-p, X=SCH$_2$C(CH$_3$)$_2$CH$_2$OC(=O)Ph
3m, $R_4$=OC(=O)NHC$_6$H$_4$Br-p, X=S(O)$_2$CH$_2$C(CH$_3$)$_2$CH$_2$OC(=O)Ph
3n, $R_4$=OC(=O)NHC$_6$H$_4$Br-p, X=S-(2-(5-methyl-1,3,4-thiadiazolyl))
3p, $R_4$=OC(=O)NHC$_6$H$_4$Br-p, X=N$^+$(CH$_3$)$_2$CH$_2$CH$_2$OH, OTs
3q, $R_4$=OC(=O)NHC$_6$H$_4$Br-p, X=NHCH$_2$C(CH$_3$)$_2$CH$_2$OH
3r, $R_4$=OH, X=CN
3s, $R_4$=OH, X=COOH
3t, $R_4$=OH, X=C(=O)N(CH$_3$)OCH$_3$
3u, $R_4$=OH, X=C(=O)NHCH$_2$C(CH$_3$)$_2$CH$_2$OH
3v, $R_4$=OC(CH$_3$)$_3$, X=OTs
3w, $R_4$=OC(CH$_3$)$_3$, X=I
3x, $R_4$=OC(CH$_3$)$_3$, X=P(O)(O-i-Pr)$_2$
3y, $R_4$=OCH$_2$Ph, X=CHO
3z, $R_4$=OCH$_2$Ph, X=C(=O)CH2C(CH3)2OH appropriate acylating agent, such as 4-bromophenyl isocyanate to produce thioether carbamate 3d. Reaction of a thioether such as 3d with an oxidant, for example, 3-chloroperoxybenzoic acid, yields a sulfone, e.g. 3e, or the corresponding sulfoxide.

Alternatively, hydrindane thioethers can be formed by reacting a hydrindane thiol, e.g. 3f, with an alkylating agent.

For example, use of isobutylene oxide, gives thioether 3g. Thiol 3f can be prepared via cleavage of benzyl thioether 3c, using, for example, sodium in liquid ammonia.

Tosylate 3b can be treated with an appropriate acylating agent, such as 4-bromophenyl isocyanate to produce the tosyloxy carbamate 3h. Displacement of the tosyl group of 3h with a thiolcarboxylate salt, such as potassium thiolacetate, followed by cleavage of the acetyl group, provides thiol carbamate 3j.

Thiol carbamate 3j can be alkylated on sulfur to provide various hydrindane thioethers. For example, treatment of 3j with 3-bromo-(2,2-dimethyl)propyl benzoate (prepared from 5,5-dimethyl-2-phenyl-1,3-dioxane according to the method of Hanessian, *Org. Synth.* 65:243 (1987), and potassium tert-butoxide in dimethyl sulfoxide solution yields thioether 3k, which can be oxidized as above to sulfone 3m, or the corresponding sulfoxide.

Reaction of tosylate 3h with a heterocyclic thiol, e.g., 2-mercapto-5-methyl-1,3,4-thiadiazole, produces heterocyclic thioethers of hydrindanes, such as 3n.

Hydrindane quaternary ammonium salts, such as 3p, can be made by reacting tosylate 3h with a tertiary amine, in this case 2-(N,N-dimethylamino)ethanol. Use of a primary amine leads instead to secondary amino compounds, e.g., 3q.

Hydrolysis of the known nitrile 3r (prepared from tosylate 3b: P. M. Wovkulich et al., cited above) provides carboxylic acid 3s, which can be converted into hydrindane amides such as 3t and 3u by treatment with an amine such as N,O-dimethylhydroxylamine or 3-amino-2,2-dimethylpropanol, respectively, in the presence of a coupling reagent, for example, a 1,3-dialkyl carbodiimide such as 1-ethyl-3-(dimethylaminopropyl) carbodiimide hydrochloride.

Hydrindane phosphonic acid derivatives, e.g., 3x, can be prepared from primary halo compounds such as iodide 3w, using Arbusov reaction conditions such as those described by Karanewsky et al., *J. Med. Chem.*, 33:2952 (1990); this reference also teaches methods for converting dialkyl phosphonates to other phosphorus compounds such as monoalkyl phosphonates, phosphinates and phosphonamides.

Hydrindane ketones, e.g., 3z, can be prepared in a variety of ways. For example, reaction of known hydrindane aldehyde 3y (Johnson et al., *J. Org. Chem.*, 50:2598 (1985) ) with an organometallic reagent, for example, that derived from isobutylene oxide by the method of Cohen et al., *J. Org. Chem.* 55:1528 (1990), followed by oxidation of the intermediate secondary alcohols with, e.g., a chromium (VI) reagent, provides ketone 3z. Other methods of preparing ketones are well known in the art, for example, reaction of organolithium reagents with N-alkoxy-N-alkyl amides such as 3t, or with acids such as 3s.

Without being bound by any theory, it is believed that angiostatic agents work by inhibiting one or more steps in the process of neovascularization, regardless of the cause; therefore the angiostatic substituted hydrindanes of this invention are useful in the treatment and prevention of neovascularization associated with a variety of diseases and surgical complications. The formation of new blood vessels (i.e. angiogenesis) is a natural developmental process; however, once a tissue has formed, there is generally no need for additional new blood vessels. A number of diseases are characterized by the growth of new blood vessels, and these diseases can be effectively treated through the inhibition of neovascularization (Doctrow & Kulakowski, "Angiogenesis modulators—New drugs for controlling blood vessel growth?," *Drug News & Perspectives* 2:74–81, March 1989; Malone & Sharpe, "Development of angiogenesis inhibitors for clinical applications," *Trends in Pharmaceutical Sciences*, 11:457–461, November 1990). Many different substances have been found to induce and promote neovascularization (Folkman, et al., "Angiogenic factors," *Science* 235:442–447, 1987; BenEzra, "Neovasculogenic ability of prostaglandins, growth factors and synthetic chemoattractants," *American J. Ophthalmology*, 86:445–461, October 1978). Inhibition may differ in the various neovascular diseases; however, it is believed that once initiated, the basic process of neovascularization is similar in all tissues regardless of the associated disease (Furcht, "Critical factors controlling angiogenesis: cell products, cell matrix and growth factors," *Laboratory Investigation*, 55:505–509, 1986).

The substituted hydrindanes of the present invention can be used in treating neovascularization associated with, for example: cancer, solid tumors, arthritis, diabetes, arteriosclerosis, angiofibroma, arteriovenous malformations, corneal graft neovascularization, delayed wound healing, diabetic retinopathy, age related macular degeneration, granulations, burns, hemangioma, hemophilic joints, hypertrophic scars, neovascular glaucoma, nonunion fractures, Osier-Weber Syndrome, psoriasis, pyogenic granuloma, retrolental fibroplasia, pterygium, scleroderma, trachoma, vascular adhesions, ocular neovascularization, parasitic diseases, hypertrophy following surgery, inhibition of hair growth, inhibition of ovulation and corpus luteum formation and inhibition of embryo implantation and development in the uterus.

In particular, these compounds are useful in preventing and treating any ocular neovascularization, including, but not limited to: retinal diseases (diabetic retinopathy, chronic glaucoma, retinal detachment, sickle cell retinopathy, age related macular degeneration); rubeosis iridis; inflammatory diseases; chronic uveitis; neoplasms (retinoblastoma, pseudoglioma); Fuchs' heterochromic iridocyclitis; neovascular glaucoma; corneal neovascularization (inflammatory, transplantation, developmental hypoplasia of the iris); neovascularization resulting following combined vitrectomy and lensectomy; vascular diseases (retinal ischemia, choroidal vascular insufficiency, choroidal thrombosis, carotid artery ischemia); pterigium; neovascularization of the optic nerve; and neovascularization due to penetration of the eye or contusive ocular injury.

The substituted hydrindanes of the present invention can be incorporated into various formulations for delivery. The type of formulation (topical or systemic) will depend on the site of disease and its severity. These compounds can be systemically delivered orally in a tablet or capsule form or by parenteral injection. The compounds can be formulated into gels, ointments, or creams for topical administration to the skin. For administration to the eye, topical formulations can be used and can include ophthalmically acceptable preservatives, surfactants, viscosity enhancers, buffers, sodium chloride, and water to form aqueous sterile ophthalmic solutions and suspensions. In order to prepare sterile ophthalmic ointment formulations, an angiostatic substituted hydrindane is combined with a preservative in an appropriate vehicle, such as mineral oil, liquid lanolin, or white petrolatum. Sterile ophthalmic gel formulations comprising the angiostatic substituted hydrindanes of the present invention can be prepared by suspending an angiostatic hydrindane in a hydrophilic base prepared from a combination of, for example, Carbopol® 940 (a carboxy vinyl polymer available from BF Goodrich Company), according to published formulations for analogous ophthalmic preparations. Preservatives and antimicrobial agents can also be incorporated in such gel formulations. Angiostatic substituted hydrindanes can also be formulated for sterile ophthalmic intraocular injections. Systemic formulations for treating ocular neovascularization can also be used, for example, orally ingested tablets and parenteral injections.

The specific type of formulation selected will depend on various factors, such as the angiostatic substituted hydrindane (or its salt or ester) being used, the dosage frequency and the severity and the location of the disease. For ocular neovascular diseases, topical ophthalmic aqueous solutions, suspensions, ointments and gels are the preferred dosage forms for the treatment of neovascularization of the front of the eye (e.g. the cornea, iris, trabecular meshwork) or the back of the eye if the angiostatic agent can be formulated such that it can be delivered topically and penetrate the tissues of the front of the eye to get to the back of the eye. The angiostatic agent will normally be contained in these formulations in an amount from about 0.0001 to 1 weight percent. For topical ocular administration, these formulations are delivered to the surface of the eye one to six times a day, depending on the discretion of the skilled clinician. Systemic administration, for example in the form of tablets, is particularly useful in the treatment of neovascularization of the back of the eye, such as the retina. Tablets containing 1–2000 mg of the angiostatic agent can be taken 1–4 times per day depending on the discretion of the skilled clinician.

The substituted hydrindanes of this invention are also useful in controlling intraocular pressure associated with primary open angle glaucoma (POAG) and in controlling the rise in intraocular pressure sometimes associated with the use of glucocorticoids.

The formulations set forth in the following examples for topical ocular suspensions, intraocular injections, and oral tablets can be prepared according to procedures known to those skilled in the art of formulating drugs.

EXAMPLE 1

Topical Ocular Suspension

|  | Amount (wt %) |
|---|---|
| Substituted hydrindane | 0.001–1.0 |
| Tyloxapol | 0.01 to 0.05 |
| HPMC | 0.5 |
| Benzalkonium chloride | 0.01 |
| Sodium Chloride | 0.8 |
| Edetate disodium | 0.01 |
| NaOH/HCl | q.s. pH 7.4 |
| Purified water | q.s. 100 ml |

EXAMPLE 2

Formulation for Sterile Intraocular Injection

Each mL contains:
| | |
|---|---|
| Substituted hydrindane | 0.01–10.0 mg |
| Sodium chloride | 7.14 mg |
| Potassium chloride | 0.38 mg |
| Calcium chloride dihydrate | 0.154 mg |
| Magnesium chloride dihydrate | 0.20 mg |
| Dried sodium phosphate | 0.42 mg |
| Sodium bicarbonate | 2.1 mg |
| Dextrose | 0.92 mg |
| NaOH/HCl | q.s. pH 7.2 |
| Purified water for injection | q.s. 1 mL |

EXAMPLE 3

Formulation for Tablet

1–2000 mg of substituted hydrindane with inactive ingredients such as starch, lactose and magnesium stearate can be formulated according to procedures known to those skilled in the art of tablet formation.

EXAMPLES 4–6

Angiostatic Activity for 3 Classes of Compounds

Angiostatic activity of the test compounds was evaluated in the chicken embryo chorioallantoic membrane (CAM) model of neovascularization as described by McNatt et al. Briefly, 1.0 ng of the indicated substituted hydrindane was added to a 10 μL bead containing 1% agarose and liposomes (2.5% dimyristoyl phosphatidyl choline) and placed on the CAM of a shell-less, 5–6 day chick embryo. After an additional 2 days of incubation at 37° C., the zone of avascularity surrounding the dose bead was evaluated. Angiostatic activity is expressed as the angiostatic response frequency per nmole of test compound.

| Example | Compound Class | Class Representative Evaluated | Angiostatic Factor (Response Frequency/nmole) |
|---|---|---|---|
| 4 | Angiostatic steroid | Tetrahydrocortisol | 2 |
| 5 | Vitamin D analogs | Calcitriol | 23,000 |
| 6 | Substituted hydrindanes | De-A,B-cholestan-8β,23S,25R,26-tetrol | 33,000 |

EXAMPLES 7–23

Angiostatic Activity of Substituted Hydrindanes Evaluated in Chick Embryo Model of Neovascularization A number of compounds of Formula II were prepared and evaluated in the CAM model as in Examples 4–6 above. Angiostatic activity results for these compounds are shown in the table below. Angiostatic activity is expressed as the angiostatic response frequency per nmole of test compound relative to positive and negative controls.

| EXAMPLE | COMPOUND | R.A.F.* |
|---|---|---|
| 7. | De-A,B-26-(benzoyloxy)-25-methyl-23-thiacholestan-8β-ol-23-dioxide-8β-(4-bromophenyl) carbamate | 3.14 |
| 8. | De-A,B-24-phenyl-23-thiacholan-8β-ol-23-dioxide-8β-(4-bromophenyl) carbamate | 2.91 |
| 9. | De-A,B-23-thiacholestan-8β,25-diol-23-dioxide-8β,25-bis(4-bromophenyl) carbamate | 2.80 |
| 10. | De-A,B-23,24-dinor-22-(tosyloxy)cholan-8β-ol-(4-bromophenyl) carbamate | 2.18 |
| 11. | De-A,B-23,24-dinor-22-(carbethoxymethyl)thiocholan-8β-ol-(4-bromophenyl) carbamate | 1.97 |
| 12. | De-A,B-23,24-dinor-22-(2-(1-methylimidazolyl)thio)-cholan-8β-ol-(4-bromophenyl) carbamate | 1.83 |
| 13. | De-A,B-23-thiacholestan-8β,25-diol-8β,25-bis(4-bromophenyl) carbamate | 1.75 |
| 14. | De-A,B-23,24-dinor-22-(2-(5-methyl-1,3,4-thiadiazolyl-thio)-cholan-8β-ol-(4-bromophenyl) carbamate | 1.67 |
| 15. | De-A,B-23-thiacholestan-8β,25-diol-23-dioxide-8β-(4-bromophenyl) carbamate | 1.57 |
| 16. | De-A,B-cholestan-8β,23R,25S,26-tetrol | 1.54 |
| 17. | De-A,B-23,24-dinorcholan-8β,22-diol-bis(phenyl carbamate) | 1.25 |
| 18. | De-A,B-cholestan-8β,23S,25R,26-tetrol | 1.00 |
| 19. | De-A,B-cholest-25-en-8β,23S-diol | 0.85 |
| 20. | De-A,B-23,24-dinor-8β-hydroxycholan-22-(N-methyl-N-methoxy) carboxamide | 0.82 |
| 21. | De-A,B-23,24-dinor-8β-hydroxycholan-22-(N-(2,2-dimethyl-3-hydroxy)propyl) carboxamide | 0.49 |
| 22. | De-A,B-23,24-dinorcholan-8β,22-diol | 0.39 |
| 23. | D-A,B-23,24-dinor-8β-hydroxycholan-22-carboxylic acid | 0.37 |

*= relative angiostatic factor (angiostatic activity at 1 ng relative to De-A,B-cholestan-8β,23S,25R,26-tetrol)

EXAMPLES 24–42

Preparation of Substituted Hydrindanes

EXAMPLE 24

De-A,B-23,24-dinor-24-phenyl-23-thiacholan-8β-ol (3c).

Benzyl mercaptan (15 mL) was added in 2-mL portions to a stirred suspension of 5.4 g of NaH (60%, oil dispersion) in 200 mL of dry DMF under Ar, keeping T<35° C.. After evolution of $H_2$ ceased, the solution was cooled to 10° C. and a solution of tosylate 3b in 80 mL of dry DMF was added in 4 portions. The solution was stirred (to 24° C.) for 15 h, then quenched carefully with water. The mixture was poured into 1 L of water and extracted with ether and ethyl acetate. The combined organic extracts were washed with 1M NaOH (twice), water (to pH 7), brine, dried ($MgSO_4$), filtered and concentrated. The residue was purified by chromatography on silica (10%→25% EtOAc-hexane) to give 27.7 g of an oil.

NMR ($CDCl_3$) δ 0.90 (s, 3H), 1.02 (d, 3H), 1.1–2.0 (m, 14H), 2.35 (ABX, 2H), 3.68 (s, 2H), 4.05 (br s, 1H), 7.3 (br s, 5H).

EXAMPLE 25

De-A,B-24-phenyl-23-thiacholan-8β-ol-8β-(4-bromophenyl) carbamate (3d).

4-Bromophenyl isocyanate (3.07 g) was added to a stirred solution of De-A,B-23,24-dinor-24-phenyl-23-thiacholan-8β-ol (3c, 3.79 g) in 24 mL of dry pyridine under Ar. After 68 h, water (5 mL) was added and the mixture was stirred for 20 min. The mixture was diluted with ether and washed with water, 1M HCl (to pH 1), water (to pH 7), brine, dried ($MgSO_4$), filtered and concentrated. The residue was suspended in 1:3 EtOAc-hexane, eluted through a silica pad and the eluate concentrated to give 5.88 g of a foam.

NMR ($CDCl_3$): δ 0.85 (s, 3H), 1.03 (d, 3H), 1.0–2.0 (m, 13 H), 2.35 (ABX, 2H), 3.68 (s, 2H), 5.14 (br s, 1H), 6.48 (br s, 1H), 7.3 (br s, 5H), 7.35 (AB, 4H).

EXAMPLE 26

De-A,B-24-phenyl-23-thiacholan-8β-ol-23-dioxide-8β-(4-bromophenyl) carbamate (3e).

3-Chloroperoxybenzoic acid (1.98 g) was added in portions to a stirred solution of De-A,B-24-phenyl-23-thiacholan-8β-ol-8β-(4-bromophenyl) carbamate (3d, 1.97 g) in 15 mL of $CH_2Cl_2$. After 15 h, the mixture was diluted with EtOAc and washed with 1M NaOH (twice), water (to pH 7), brine, dried ($MgSO_4$), filtered and concentrated. The residue was triturated (5% ether-hexane) to give 1.89 g of a pink solid, m.p. 78°–84° C..

Anal. Calc'd: C, 59.12; H, 6.25; N, 2.55; S, 5.85. Found: C, 59.02; H, 6.28; N, 2.52; S, 5.82.

EXAMPLE 27

De-A,B-23,24-dinor-22-mercaptocholan-8β-ol (3f).

Sodium was added in 0.5-g portions to a stirred solution of De-A,B-24-phenyl-23-thiacholan-8β-ol (3c, 9.35 g) in 50 mL of dry THF and 250 mL of liquid $NH_3$ at −33° C. under Ar, until the blue color persisted (3.5 g Na added). The mixture was quenched carefully with solid $NH_4Cl$, and the excess $NH_3$ was allowed to evaporate. The residue was dissolved in ether and water, the mixture was acidified to pH 2 with 1M HCl, and partitioned between ether and water. The ethereal solution was washed with brine, dried ($MgSO_4$), filtered and concentrated to give 6.75 g of an oil.

NMR ($CDCl_3$) δ 0.94 (s, 3H), 0.99 (d, 3H), 1.0–2.0 (m, 15H), 2.5 (ABX, 2H), 4.08 (br s,1H).

EXAMPLE 28

De-A,B-23-thiacholestan-8β,25-diol (3g).

NaOCH₃ (2.4 mL of a 25% solution in $CH_3OH$) was added to a stirred solution of De-A,B-23,24-dinor-22-mercaptocholan-8β-ol (3f, 2.25 g) in 15 mL of $CH_3OH$ under Ar. Isobutylene oxide (1.49 g) was added and the solution was heated to reflux for 2 h, then cooled to 24° C. over 15 h. The mixture was poured into water, extracted with ether and ethyl acetate and the organic extracts washed with water (to pH 7), brine, dried ($MgSO_4$), filtered and concentrated. The residue was purified by chromatography on silica (25%→50% EtOAc-hexane) to give 2.47 g of a viscous oil.

NMR ($CDCl_3$) δ 0.95(s, 3H), 1.06 (d, 3H), 1.27 (s, 6H), 1.0–2.1 (m, 15H), 2.54 (ABX, 2H), 2.63 (br s, 2H), 4.08, (1 H).

EXAMPLE 29

De-A,B-23,24-dinor-22-(tosyloxy)cholan-8β-ol-(4-bromophenyl) carbamate (3h).

4-Bromophenyl isocyanate (6.35 g) was added to a stirred solution of tosylate 3b (9.40 g) in 50 mL of dry pyridine under Ar. After 2.5 h, 5 mL of water was added and stirring continued for 0.5 h. The mixture was diluted with ether and washed with water, 1M $H_2SO_4$, water (to pH 7), brine, dried ($MgSO_4$), filtered and concentrated. The residue was recrystallized from ethanol to give 10.7 g of a white solid, m.p. 159°–161° C.

Anal. Calcd: C, 57.44; H, 6.07; N, 2.48; S, 5.68. Found: C, 57.52; H, 6.12; N, 2.47; S, 5.73.

EXAMPLE 30

De-A,B-23,24-dinor-22-mercaptocholan-8β-ol-8β-(4-bromophenyl) carbamate (3j).

Potassium thiolacetate (1.75 g) was added to a stirred solution of De-A,B-23,24-dinor-22-(tosyloxy)cholan-8β-ol-(4-bromophenyl) carbamate (3h, 4.32 g) in 13 mL of dry DMF under Ar. After 70 min, the mixture was diluted with ether and ethyl acetate, washed with water (3 times), brine, dried ($MgSO_4$), filtered and concentrated, giving 3.58 g of a yellow foam. This material was dissolved in 40 mL of absolute EtOH and 20 mL of dry THF, and the solution was deoxygenated by sparging with argon. A solution of 0.85 g of NaOH in 8 mL of water was added. After 5 min, the mixture was poured into sat. $KH_2PO_4$, extracted with ether, and the ethereal solution dried ($MgSO_4$), filtered and concentrated. The residue was purified by chromatography on silica (10% EtOAc-hexane) to give 2.1 g of compound 3j as a foam.

NMR ($CDCl_3$) δ 0.90 (s, 3H), 1.03 (d, 3H), 1.1–2.1 (m, 13H), 2.50 (ABX, 2H), 5.15 (br s, 1H), 6.49 (br s, 1 H), 7.35 (AB, 4H).

EXAMPLE 31

3-bromo-(2,2-dimethyl)propyl benzoate.

N-Bromosuccinimide (20.7 g) was added to a stirred solution of 5,5-dimethyl-2-phenyl-1,3-dioxane (19.2 g) in 200 mL of $CCl_4$ containing 8.5 g of $BaCO_3$ in suspension. The mixture was heated to reflux under Ar for 2.2 h, then cooled to 24° C. over 15 h, filtered and concentrated. The residue was partitioned between ether and water, and the ethereal solution was washed with brine, dried ($MgSO_4$), filtered and concentrated to give 24.8 g of a yellow oil which was stored in the dark at 0° C. under Ar.

NMR (CDCl$_3$) δ 1.16 (s, 6H), 3.45 (s, 2H), 4.20 (s, 2H), 7.5 (m, 3H), 8.04 (dd, 2H).

EXAMPLE 32

De-A,B-26-(benzoyloxy)-25-methyl-23-thiacholestan-8β-ol-8β-(4-bromophenyl) carbamate (3k).

Potassium tert-butoxide (0.32 g) was added to a stirred solution of De-A,B-23,24-dinor-22-mercaptocholan-8β-ol-8β-(4-bromophenyl) carbamate (3j, 1.03 g) in 5.0 mL of dry DMSO under Ar. After 1 min, 3-bromo-(2,2-dimethyl) propyl benzoate (1.23 g) was added via syringe. The mixture was stirred for 2 h, then diluted with ether, washed with water (to pH 7), brine, dried (MgSO$_4$), filtered and concentrated. The residue was purified by chromatography on silica (10% EtOAc-hexane) to give 0.82 g of a foam.

NMR (CDCl$_3$) δ 0.85 (s, 3H), 1.04 (d, 3H), 1.10 (s, 6H), 1.0–2.1 (m, 13H), 2.45 (ABX, 2H), 2.60 (s, 2H), 4.16 (s, 2H), 5.19 (br s, 1H), 6.5 (s, 1H), 7.35 (AB, 4H), 7.4–7.6 (m, 3H), 8.04 (dd, 2H).

EXAMPLE 33

De-A,B-26-(benzoyloxy)-25-methyl-23-thiacholestan-8β-ol-23-dioxide-8β-(4-bromophenyl) carbamate (3m).

3-Chloroperoxybenzoic acid (0.35 g) was added in portions to a stirred solution of De-A,B-26-(benzoyloxy)-25-methyl-23-thiacholestan-8β-ol-8β-(4-bromophenyl) carbamate (3k, 0.41 g) in 16 mL of CH$_2$Cl$_2$, keeping T≦40° C. After stirring at 24° C. for 15 h, the mixture was diluted with EtOAc, washed with 1M NaOH (twice), water (to pH 7), brine, dried (MgSO$_4$), filtered and concentrated. The residue was triturated with hexane containing 2–5% ether to give (after cooling to 0° C.) 0.36 g of a white solid, m.p. 75°–78° C.

Anal. Calcd: C, 59.25; H, 6.53; N, 2.16; S, 4.94. Found: C, 59.30; H, 6.55; N, 2.12; S, 5.03.

EXAMPLE 34

De-A,B-23,24-dinor-22-(2-(5-methyl-1,3,4-thiadiazolyl) thio)cholan-8β-ol-(4-bromophenyl) carbamate (3n).

A stirred solution of 2-mercapto-5-methyl-1,3,4-thiadiazole (0.27 g), N,N-diisopropylethylamine (0.35 mL), and De-A,B-23,24-dinor-22-(tosyloxy)cholan-8β-ol-(4-bromophenyl) carbamate (3h, 0.57 g) in 2.0 mL of dry CH$_3$CN was heated to reflux under Ar for 20 min. The cooled mixture was diluted with EtOAc, washed with water, 1M HCl, water (to pH 7), brine, dried (MgSO$_4$), filtered and concentrated. The residue was recrystallized from ether-hexane to give 0.28 g of a pale yellow solid, m.p. 145°–149° C.

Anal. Calcd: C, 52.66; H, 5.77; N, 8.01. Found: C, 52.77; H, 5.78; N, 7.95.

EXAMPLE 35

De-A,B-23,24-dinor-8β-(4-bromophenylcarbamoyloxy)-22-(N,N-dimethyl-N-(2-hydroxy)ethyl)cholanammonium p-toluenesulfonate (3p).

A stirred solution of (N,N-dimethylamino)ethanol (2.5 mL) and De-A,B-23,24-dinor-22-(tosyloxy)cholan-8β-ol-(4-bromophenyl) carbamate (3 h, 0.57 g) in 5.0 mL of absolute EtOH was heated to reflux under Ar for 6 h. The cooled mixture was partitioned between ether and water. The aqueous solution was concentrated, dried azeotropically with toluene (twice) followed by EtOH (twice) and the residue was triturated with ether to give 0.38 g of a foam.

NMR (DMSO-d$_6$) δ 0.98 (s, 3H), 1.09 (d, 3H), 1.1–2.1 (m, 13H), 2.27 (s, 3H), 3.05 (s, 6H), 3.4 (m, 4H), 3.8 (br s, 2H), 5.03 (br s, 1H), 5.3 (br s, 1 H, exchanges), 7.3 (AB, 4H), 7.45 (s, 4H), 9.52 (s, 1 H, exchanges).

EXAMPLE 36

De-A,B-25-methyl-23-azacholestan-8β-26-diol-8β-(4-bromophenyl) carbamate (3q).

A stirred solution of 3-amino-2,2-dimethyl-1-propanol (1.0 g) and De-A,B-23,24-dinor-22-(tosyloxy)cholan-8β-ol-(4-bromophenyl) carbamate (3 h, 0.80 g) in 4.5 mL of dry 1,2-dimethoxyethane was heated to reflux under Ar for 6 h. The cooled mixture was diluted with EtOAc, washed with water (3 times), brine, dried (MgSO$_4$) filtered and concentrated to give 0.76 g of a foam.

NMR (DMSO-d$_6$) δ 0.75 (d, 3H), 0.77 (s, 3H), 0.79 (s, 3H), 0.91 (s, 3H), 1.0–2.5 (m, 18H), 3.16 (s, 2H), 5.02 (br s, 1H), 7.45 (s, 4H), 9.48 (s, 1 H, exchanges).

EXAMPLE 37

De-A,B-23,24-dinor-8β-hydroxycholan-22-carboxylic acid (3s).

A stirred suspension of nitrile 3r (6.57 g) and 6.7 g of KOH pellets in 80 mL of ethylene glycol was heated to 160° C. under Ar for 17 h. The base-soluble product was isolated giving 6.15 g of a solid. A sample was recrystallized from n-BuCl: m.p. 129.5°–131° C.

Anal. Calcd: C, 69.96; H, 10.07 Found: C, 69.86; H, 10.13.

EXAMPLE 38

De-A,B-23,24-dinor-8β-hydroxycholan-22-(N-methyl-N-methoxy)carboxamide (3t).

1-Ethyl-3-(dimethylaminopropyl)carbodiimide hydrochloride (1.15 g) was added to a stirred solution of acid 3s (0.95 g), N,N-diisopropylethylamine (1.05 mL) and N,O-dimethylhydroxylamine hydrochloride (0.59 g) in CH$_3$CN (2.0 mL) and CH$_2$Cl$_2$ (2.0 mL) under Ar. After 16 h, the mixture was diluted with EtOAc, extracted with 1M H$_2$SO$_4$, water (twice), brine, dried (MgSO$_4$), filtered and concentrated. The residue was crystallized (hexane—n-BuCl) to give 0.45 g of white crystals, m.p. 91°–94° C.

Anal. Calcd: C, 67.81; H, 10.31; N, 4.94. Found: C, 67.89; H, 10.35; N, 4.90.

EXAMPLE 39

De-A,B-23,24-dinor-8β-hydroxycholan-22-(N-(2,2-dimethyl-3-hydroxy)propyl) carboxamide (3u).

1-Ethyl-3-(dimethylaminopropyl)carbodiimide hydrochloride (0.30 g) was added to a stirred solution of acid 3s (0.26 g) and 3-amino-2,2-dimethyl-1-propanol (0.15 g) in 1.0 mL of dry CH$_3$CN and 1.0 mL of dry CH$_2$Cl$_2$ under Ar. After 2 h, the mixture was diluted with EtOAc, washed with water, 1M H$_2$SO$_4$ (to pH 1), water (to pH 7), brine, dried (MgSO$_4$), filtered and concentrated. The residue was recrystallized from n-BuCl-EtOAc to give 0.22 g of white crystals, m.p. 172.5°–175° C.

Anal. Calcd: C, 70.11; H, 10.84; N, 4.30. Found: C, 70.12; H, 10.85; N, 4.23.

EXAMPLE 40

De-A,B-23,24-dinor-22-(tosyloxy)-8β-(tert-butoxy)cholane (3v).

Isobutylene (40 mL) was condensed into a stirred, cooled (−78° C.) solution of tosylate 3b (3.66 g) in 25 mL of dry CH₂Cl₂ under Ar. Phosphoric acid (0.25 mL, dried with P₂O₅) was added, followed by 0.40 mL of BF₃ etherate. The solution was stirred overnight while warming to 24° C. and the excess isobutylene was allowed to evaporate through a drying tube. The solution was poured into 2M NH₄OH, extracted with ether, and the organic extracts washed with water (to pH 9), brine, dried (MgSO₄), filtered and concentrated. The residue was purified by chromatography on silica (20% ether-hexane) to give 3.63 g of a viscous oil.

NMR (CDCl₃) δ 0.82 (s, 3H), 0.94 (d, 3H), 1.09 (s, 9H), 0.9–1.9 (m, 13H), 3.74 (br s, 1H), 3.9 (ABX, 2H), 7.35 (d, 2H), 7.8 (d, 2H).

EXAMPLE 41

Diisopropyl De-A,B-23,24-dinor-8β-tert-butoxycholan-22-phosphonate (3x).

(A) A solution of NaI (2.7 g) and De-A,B-23,24-dinor-22-(tosyloxy)-8β-(tert-butoxy)cholane (3v, 3.62 g) in 40 mL of 2-butanone was heated to reflux under Ar for 45 min, then cooled to 24° C. for 15 h. The mixture was diluted with ether, washed with water, 2M Na₂S₂O₃, water and brine, dried (MgSO₄), filtered and concentrated to give 3.10 g of De-A,B-23,24-dinor-22-iodo-8β-(tert-butoxy)cholane (3w), m.p. 84°–89° C. The analytical sample, m.p. 89°–91° C., was secured by recrystallization from methanol.

Anal. Calcd: C, 53.97; H, 8.26. Found: C, 54.08; H, 8.27.

(B) A solution of 3w (2.85 g) and triisopropyl phosphite (21 mL) was stirred and heated to 150° C. under Ar for 1.5 h. The excess triisopropyl phosphite was removed by rotary evaporation (100° C., ~1 mmHg) and the residue was purified by chromatography on silica (25% EtOAc-hexane) to give 2.65 g of 3x as an oil.

NMR (CDCl₃) δ 5 0.89 (s, 3H), 1.10 (s, 9H), 1.12 (d, 3H), 1.31 (dd, 12H); 1.0–2.0 (m, 15H), 3.75 (br s, 1H), 4.7 (m, 2H). NMR (³¹P, CDCl₃) δ 30.52.

EXAMPLE 42

De-A,B-8β-(benzyloxy)-23-oxocholestan-25-ol (3z).

Lithium wire (1% Na) (0.21 g) was added in 0.2-cm portions to a stirred, ice-cooled solution of 4,4′-di-t-butylbiphenyl (8.5 g) in 90 mL of anhydrous THF under Ar. After stirring vigorously for 5.5 h, the deep blue-green solution was cooled to −70° C. Isobutylene oxide (1.35 g) was added via syringe, keeping T <−65° C. After 6 min, a solution of De-A,B-23,24-dinor-8β-(benzyloxy)cholan-22-carboxaldehYde (3y, 2.41 g) in 10 mL of anhydrous THF was added rapidly. The stirred mixture was allowed to warm to 8° C. over 4 h, and was then quenched with sat. KH₂PO₄ and stirred for 15 h. The phases were separated and the aqueous solution was extracted with ether. The combined organic extracts were dried (MgSO₄), filtered and concentrated. The residue was purified by chromatography on silica to give 2.14 g of a viscous oil. Pyridinium chlorochromate (PCC) (0.85 g) was added to a stirred solution of 0.60 g of this oil in 25 mL of dry CH₂Cl₂. After 3 h, a 0.89-g portion of PCC was added, and stirring was continued for 15 h. The mixture was eluted through Florisil with ether, and the concentrated eluate was purified by chromatography on silica (25% EtOAc-hexane) to give 0.36 g of the title compound as an oil.

NMR (DMSO-d₆) δ 0.81 (d, 3H), 0.90 (s, 3H), 1.12 (s, 6H), 1.2–2.0 (m, 13H), 2.3 (ABX, 2H), 2.45 (m, 2H), 3.63 (br s, 1H), 4.4 (AB, 2H), 4.60 (s, 1H), exchanges), 7.30 (s, 5H)

We claim:

1. A substituted hydrindane having the formula

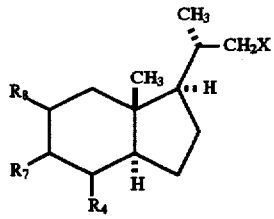

where X is C(OH)R₁R₁, C(OR₁)R₁R₁, C(OR₂)R₁R₁, C(OH)R₁R₂, C(OR₁)R₁R₂, C(OR₂)R₁R₂, C(OH)R₂R₂, C(OR₁)R₂R₂, C(OR₂)R₂R₂, S(=O)ₙH, S(=O)ₙR₁, SR₂, P(=O)R₁R₁, P(=O)(OH)₂, P(=O)(OH)(OR₁), P(=O)(OR₁)(OR₁), P(=O)(OH)(NH₂), P(=O)(OR₁)(NH₂), P(=O)(OH)(NHR₁), P(=O)(OH)(NR₁R₁), P(=O)(OR₁)(NHR₁) P(=O)(OR₁)(NR₁R₁), NH₂, NHR₁, NHR₂, NR₁R₁, NR₁R₂, NHOH, N(OH)R₁, N(OH)R₂, NH(OR₁), NH(OR₂), N(OR₁)R₂, N(OR₂)R₁, N(OR₂)R₂, N(OR₁)R₁, ⊕S(R₁)(₁) Q⊖, ⊕N(R₁)R₁)(R₁) Q⊖ wherein Q⊖ is a halide, sulfonate, or carboxylate anion; C(=O)R₁, C(=O)R₂, C(=O)NH₂, C(=O)NHR₁, C(=O)NR₁R₁, C(=O)N(OH)R₁, C(=O)N(OR₁)OR₁, C(=O)N(OR₂)R₁;

n=0, 1 or 2;

R₁ is aryl, haloaryl, C₁–C₁₀ alkyl, branched alkyl, cycloalkyl, aralkyl, carboxyalkyl or haloalkyl, optionally unsaturated and/or substituted with up to 6 OH, 6 OR₃, or 6 OR₂; or imidazolyl, triazolyl, thiadiazolyl, oxadiazolyl, thiazolyl, isothiazolyl, oxazolyl, isoxazolyl, or pyridyl, optionally substituted with up to three halogen or C₁–C₆ alkyl groups;

R₂ is C(=O)H, C(=O)R₁, C(=O)OR₁, C(=O)OH, C(=O)NH₂ C(=O)NHR₁, C(=O)NR₁R₁;

R₃ is aryl, haloaryl, C₁–C₁₀ alkyl, branched alkyl, cycloalkyl, aralkyl, carboxyalkyl or haloalkyl optionally unsaturated and/or substituted with up to 6 OH;

R₄ is H, OR₂, OR₁, OH, =NOH, =NOR₁, =NOR₂; and provided that if X is S(O)₂(optionally substituted phenyl) then R₄≠OH; and R₇ and R₈ are H or together are optionally a double bond; and wherein aryl denotes phenyl, naphthyl, furyl, thienyl, pyridyl, benzofuryl, indolyl, benzothienyl, quinolyl or iso-quinolyl;

R₁R₁ attached to the same C, S, P or N atom can form a ring of from 3 through 7 members; and for those substituents containing more than one R₁, R₂ or R₃, each R₁, R₂, or R₃ may be the same or different; or a pharmaceutically acceptable salt or ester thereof.

2. A substituted hydrindane according to claim 1 wherein the hydrindane has the formula

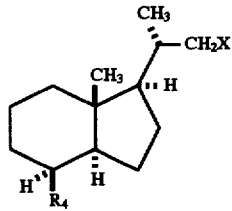

where X is C(OH)R₁R₁, C(OR₁)R₁R₁, C(OR₂)R₁R₁, C(OH)R₁R₂, C(OR₁)OR₁R₂, C(OR₂)R₁R₂, C(OH)R₂R₂, C(OR₁)R₂R₂, C(OR₂)R₂R₂, S(=O)ₙH, S(=O)ₙR₁, SR₂, P(=O)R₁R₁, P(=O)(OH)₂, P(=O)(OH)(OR₁), P(=O)(OR₁)

(OR$_1$), P(=O)(OH)(NH$_2$), P(=O)(OR$_{10}$)(NH$_2$), P(=O)(OH)(NHR$_1$), P(=O)(OH)(NR$_1$R$_1$), P(=O)(OR$_1$)(NHR$_1$)P(=O)(OR$_1$)(NR$_1$R$_1$), NH$_2$, NHR$_1$, NHR$_2$, NR$_1$R$_1$, NR$_1$R$_2$, NHOH, N(OH)R$_1$, N(OH)R$_2$, NH(OR$_1$), NH(OR$_2$), N(OR$_1$)R$_2$, N(OR$_2$)R$_1$, N(OR$_2$)R$_2$, N(OR$_1$)R$_1$, $^{\oplus}$S(R$_1$)(R$_1$) Q$^{\ominus}$, $\oplus$N(R$_1$)(R$_1$)(R$_1$) Q$^{\ominus}$ wherein Q$^{\ominus}$ is a halide, sulfonate, or carboxylate anion; C(=O)R$_1$, C(=O)R$_2$, C(=O)NH$_2$, C(=O)NHR$_1$, C(=O)NR$_1$R$_1$, C(=O)N(OH)R$_1$, C(=O)N(OR$_1$)R$_1$, C(=O)N(OR$_2$)R$_1$; and R$_4$ is H, OR$_2$, OR$_1$, OH, =NOH, =NOR$_1$, =NOR$_2$; and provided that if X is S(O)$_2$(optionally substituted phenyl) then R$_4$≠OH.

3. A substituted hydrindane according to claim 2 wherein the hydrindane is selected from the group consisting of De-A,B-26-(benzoyloxy)-25-methyl-23-thiacholestan-8β-ol-23-dioxide-8β-(4-bromophenyl) carbamate, De-A,B-24-phenyl-23-thiacholan-8β-ol-23-dioxide-8β-(4-bromophenyl) carbamate, and De-A,B-23-thiacholestan-8β,25-diol-23-dioxide-8β,25-bis(4-bromophenyl) carbamate.

4. A process for preparing 3-bromo-(2,2-dimethyl)propyl benzoate which comprises the step of reacting 5,5-dimethyl-2-phenyl-1,3-dioxane with N-bromosuccinimide in an inert solvent.

* * * * *